United States Patent [19]

Zinnen

[11] Patent Number: 4,827,077
[45] Date of Patent: May 2, 1989

[54] SEPARATION OF INDENE FROM ALKYL AROMATICS

[75] Inventor: Hermann A. Zinnen, Evanston, Ill.

[73] Assignee: UOP Inc., Des Plaines, Ill.

[21] Appl. No.: 165,192

[22] Filed: Feb. 22, 1988

[51] Int. Cl.$^4$ ................................................ C07C 7/12
[52] U.S. Cl. .................................... 585/820; 585/828; 208/310 Z
[58] Field of Search .............................. 585/820, 828; 208/310 Z

[56] References Cited

U.S. PATENT DOCUMENTS

| | | | |
|---|---|---|---|
| 2,882,244 | 4/1959 | Milton | 252/455 |
| 2,930,821 | 3/1960 | Schwoegler et al. | 260/674 |
| 2,967,896 | 1/1961 | Fleck et al. | 585/828 |
| 3,130,007 | 4/1964 | Breck | 23/113 |
| 3,133,126 | 5/1964 | Fleck et al. | 208/310 Z |
| 3,668,267 | 6/1972 | Hedge | 208/310 Z |
| 3,888,939 | 6/1975 | Rosback | 260/677 |
| 4,469,913 | 9/1984 | Dessau | 208/310 Z |

OTHER PUBLICATIONS

Jean et al., Preprint Papers A. Chem. Soc., Div. Fuel Chem. 32(3), 262-5 (CA 105 (12): 100117y).
Kondratov et al. Zh. Fiz. Khim., 50(3) 801 (CA 84 (24): 170137b).
Kondratov et al., Koks Khim. (9) 39-43 (CA 90 (5): 38709j).
Vykhristyuk et al., Koks Khim. (2) 38-41 (CA 94: 208588w).

Primary Examiner—Patrick P. Garvin
Assistant Examiner—E. D. Irzinski
Attorney, Agent, or Firm—Thomas K. McBride; John F. Spears, Jr.; Jack H. Hall

[57] ABSTRACT

The chromatographic adsorption separation of indene from petrochemical or synthetic feed mixtures with an Na- or K-exchanged X- or Y-zeolite and toluene, benzene, fluorobenzene or other halogen- or alkyl-substituted monocyclic aromatic desorbents. Selectivity of the separation is dependent on water content, from 1–8% (wt.), of the adsorbent.

10 Claims, 9 Drawing Sheets

SEPARATION OF INDENE FROM ALKYL AROMATICS

FIELD OF THE INVENTION

The field of art to which this invention pertains is solid-bed adsorptive separation, more specifically, to an improved process for separating indene from a petrochemical feed material or synthetic mixtures containing indene.

BACKGROUND OF THE INVENTION

Indene has been used in the preparation of synthetic resins, e.g., coumarone-indene resins, but more recently has found use as a comonomer in other resins and, in high purity, as a monomer to improve the surface properties of polymers with minimal loss to vaporization by virtue of its high vapor pressure.

Previous methods for obtaining high purity indene include centrifugation, distillation and crystallization of indene-rich naphtha-cracker pyrolysis oil.

A number of publications exist which relate to removal of impurities from various petroleum fractions, e.g., naphtha, naphthalene, etc. These references indicate group selectivity for a number of impurities including indene, but are not highly selective for indene alone. Furthermore, they do not teach any means for recovering indene from the adsorbent. In the present invention, the selection of a desorbent to recover indene alone is an important step in that it is necessary to remove other less strongly adsorbed feed components before desorbing indene. For example, reference is made to: Jean et al. Preprint Papers A. Chem. Soc., Div Fuel Chem. 32 (3), 262-5 (CA 105 (12): 100117y); Kondratov et al. Zh. Fiz. Khim., 50(3), 801 (CA 84 (24): 170137b); Kondratov et al., Koks Khim. (9) 39–43 (CA 90 (5): 38709j).

An article by Vykhristyuk et al., Koks Khim. (2) 38–41 (CA 94: 208588w) discloses the removal of a number of impurities from naphthalene by treating with NaX zeolite adsorbent. Again, the authors are interested in removing small amounts of all types of impurities from a fuel and do not deal with recovering the impurities or with recovering indene from the remaining contaminants.

It is an object of this invention, however, to obtain indene in highly purified form by highly selective chromatographic adsorption separation process from mixtures, including petrochemicals, such as crude oil fractions, e.g., naphtha, naphthalene; processed mixtures, e.g., naphtha cracker pyrolysis oil; synthetically-produced mixtures, e.g., dehydrogenation or cyclization reactions containing aromatics, etc., which cannot be separated easily and economically by other conventional means.

It is a further object to provide a desorbent which will selectively desorb the indene from the adsorbent with sufficient resolution so as to obtain indene product with substantially reduced impurities and other feed materials. The preferred desorbent is toluene, but benzene and fluorobenzene and other liquid alkyl- or halogen-substituted monocyclic aromatics are suitable for use in the process.

It is further believed that the crystallization process described previously could be much more efficient and economical if the product of this invention were used as the feed material, thereby reducing the overall cost of achieving very high purity indene.

SUMMARY OF THE INVENTION

In brief summary, the invention is, in a primary embodiment, a process for separating indene from a feed mixture comprising a petroleum fraction or a synthetically produced mixture containing indene, which comprises contacting the mixture at adsorption conditions in an indene adsorption zone with an adsorbent exhibiting selectivity for the indene comprising a type X or type Y zeolite, the exchangeable cationic sites of which are exchanged with sodium or potassium ions, thereby selectively adsorbing the indene thereon and thereafter recovering an indene-rich extract. The water content of the above X-type adsorbents play an important part in the economics and purity of recovery of indene by the process. Concentrations of from 1-8% are acceptable, but for economy of operation, the amount of water must be balanced between selectivity, which increases as the concentration decreases, and desorbent flow, which decreases as the water concentration increases. The optimum concentration appears to be in the range of 4-7% in order to achieve the maximum selectivity with the lowest desorbent rate for recovering indene alone and also to reject from the feedstock the numerous other close-boiling materials of similar structure contained within the aforesaid feedstocks.

Other embodiments of the invention encompass details about feed mixtures, adsorbents, desorbent materials and operating conditions, all of which are hereinafter disclosed in the following discussions of each of the facets of the present invention.

DETAILED DESCRIPTION OF THE INVENTION

This invention relates to a process for separating indene from indene feed materials by adsorption chromatography, utilizing Na-or K-exchanged X or Y zeolites, in conjunction with an appropriate desorbent, preferably followed by a step for separating and recovering the useful materials from the raffinate of the indene separation process.

For purposes of this invention, the various terms which are hereinafter used may be defined in the following manner.

A "feed mixture" is a mixture containing one or more extract components and one or more raffinate components to be separated by the process. The term "feed stream" indicates a stream of a feed mixture which passes to the adsorbent used in the process.

An "extract component" is a compound or type of compound that is more selectively adsorbed by the adsorbent while a "raffinate component" is a compound or type of compound that is less selectively adsorbed. The term "desorbent material" shall mean generally a material capable of desorbing an extract component. The term "desorbent stream" or "desorbent input stream" indicates the stream through which desorbent material passes to the adsorbent. The term "raffinate stream" or "raffinate output stream" means a stream through which a raffinate component is removed from the adsorbent. The composition of the raffinate stream can vary from essentially 100% desorbent material to essentially 100% raffinate components. The term "extract stream" or "extract output stream" shall mean a stream through which an extract material which has been desorbed by a desorbent material is removed from the adsorbent. The composition of the extract stream, likewise, can vary from essentially 100% desorbent material to essentially 100% extract components. At least a portion of the extract stream and preferably at least a portion of the raffinate stream from the separation process are passed to separation means, typically fractionators, where at least a portion of desorbent material is separated to produce an extract product and a raffinate product. The terms "extract product" and "raffinate product" mean products produced by the process containing, respectively, an extract component and a raffinate component in higher concentrations than those found in the extract stream and the raffinate stream.

The adsorbents which are employed by this invention to selectively adsorb indene from petrochemical mixtures comprise the type X and type Y crystalline aluminosilicates or zeolites which are described as a three-dimensional network of fundamental structural units consisting of silicon-centered $SiO_4$ and aluminum-centered $AlO_4$ tetrahedra interconnected by a mutual sharing of optical oxygen atoms. The space between the tetrahedra is occupied by water molecules and subsequent dehydration or partial dehydration results in a crystal structure interlaced with channels of molecular dimension.

Thus, the crystalline aluminosilicates are often referred to as molecular sieves and separations performed with molecular sieves are generally thought to take place by a physical "sieving" of smaller from larger molecules appearing in the feed mixture. In the separation of indene from complex petrochemical mixtures, however, the separation apparently occurs because of differences in physical chemical attraction of the different components and the adsorbent rather than on pure physical size differences in the molecules.

In hydrated form, the preferred crystalline aluminosilicates generally encompass those zeolites represented by the formula 1 below:

$$M_{2/n}O:Al_2O_3:wSiO_2:yH_2O$$

where "M" is a cation which balances the electrovalence of the tetrahedra and is generally referred to as an exchangeable cationic site, "n" represents the valence of the cation, "w" represents the moles of $SiO_2$, and "y" represents the moles of water. The cations may be any one of a number of cations which will hereinafter be described in detail.

Adsorbents comprising the type X structured and type Y structured zeolites are especially preferred for the adsorptive separation of indene. These zeolites are described and defined in U.S. Pat. Nos. 2,882,244 and 3,130,007, respectively. The terms "type X-structured" and "type Y-structured" zeolites as used herein shall include all zeolites which have general structures as represented in the above two cited patents.

The type X- and Y-structured zeolites in the hydrated or partially hydrated form can be represented in terms of moles of metal oxides as shown in Formulas 2 and 3, respectively, below:

Formula 2

$$(0.9\pm0.2)M_{2/n}O:Al_2O_3:(2.5\pm0.5)SiO_2:yH_2O$$

Formula 3

$$(0.9\pm0.2)M_{2/n}O:Al_2O_3:wSiO_2:yH_2O$$

where "M" represents at least one cation having a valence of not more than 3, "n" represents the valence of "M", "w" is greater than 3.0 up to about 6 and "y" is a value up to about 9 depending upon the identity of "M" and the degree of hydration of the crystal.

The terms "type X zeolite" and "type Y zeolite" as employed herein shall refer not only to a type X-structured and type Y-structured zeolites containing sodium and potassium cations as the cation "M" indicated in the formulas above but also shall refer to those containing other additiona cations such as cations included in Groups IA and IIA of the Periodic Table of Elements, i.e., the alkali metals and alkaline earth metals, respectively. Typically both the type X and type Y structured zeolites as initially prepared are predominantly in the sodium form. The term "exchanged cationic site" generally refers to the site in the zeolite occupied by the cation "M". This cation, usually sodium, can be replaced or exchanged with other specific cations, such as those mentioned above, depending on the type of the zeolite to modify characteristics of the zeolite. The preferred zeolite for use in this invention is type Y ion exchanged with sodium cations.

Cations occupying exchangeable cationic sites in the zeolite are exchanged with other cations by ion exchange methods well known to those having ordinary skill in the field of crystalline aluminosilicates. Such methods are generally performed by contacting the zeolite or an adsorbent material containing the zeolite with an aqueous solution of the soluble salt of the cation or cations desired to be placed upon the zeolite. After the desired degree of exchange takes place, the sieves are removed from the aqueous solution, washed, then dried to a desired water content. By such methods, the sodium cations and any non-sodium cations which might be occupying exchangeable sites are impurities in a sodium-X or sodium-Y zeolite can be partially or essentially completely replaced with other cations. It is preferred that the zeolite used in the process of this invention contain cations at exchangeable cationic sites selected from the group consisting of the alkali metals and particularly sodium and potassium.

Typically, adsorbents used in separative processes contain zeolite crystals and amorphous material. The zeolite will typically be present in the adsorbent in amounts ranging from about 75 wt. % to about 98 wt. % based on volatile-free composition. Volatile-free compositions are generally determined after the adsorbent has been calcined at 900° C. in order to dry all volatile matter. The remainder of the adsorbent will generally be amorphous material such as silica, or silica-alumina mixtures or compounds, such as clays, which material is present in intimate mixture with the small particles of the zeolite material. This amorphous material may be an adjunct of the manufacturing process for zeolite (for example, intentionally incomplete purification of either zeolite during its manufacture) or it may be added to relatively pure zeolite but in either case its usual purpose is a as a binder to aid in forming or agglomerating the hard crystal line particles of the zeolite. Normally, the adsorbent will be in the form of particles such as extrudates, aggregates, tablets, macrospheres or granules having a desired particle size range. The zeolitic adsorbent used in this process will preferably have a particle size range of about 16–40 mesh (Standard U.S. Mesh). The adsorbent is preferably packed in a vertical column through which the feed mixture is passed, preferably downwardly.

The adsorbent of this invention has been found to possess a very high degree of adsorptive selectivity for indene as compared to other components of the petrochemical feed mixture.

In general, relative selectivity can be expressed not only for one feed compound as compared to another, but can also be expressed between any feed mixture component and the desorbent material. The selectivity, ($\beta$) as used throughout this specification is defined as the ratio of the two components of the adsorbed phase over the ratio of the same two components in the unadsorbed phase at eqiilibrium conditions. Relative selectivity is shown as Equation 1, below.

$$\text{Selectivity} = (\beta) = \frac{[\text{wt. percent } C/\text{wt. percent } D]_A}{[\text{wt. percent } C/\text{wt. percent } D]_U} \quad \text{Equation 1}$$

where C and D are two components of the feed represented in weight percent and the subscripts A and U represent the adsorbed and unadsorbed phases, respectively. The equilibrium conditions are determined when the feed passing over a bed of adsorbent does not change composition after contacting the bed of adsorbent. In other words, there is no net transfer of material occurring between the unadsorbed and adsorbed phases. Where selectivity of two components approaches 1.0 there is no preferential adsorption of one component by the adsorbent with respect to the other; they are both adsorbed (or non-adsorbed) to about the same degree with respect to each other. As the ($\beta$) becomes less than or greater than 1.0, there is a preferential adsorption by the adsorbent for one component with respect to the other. When comparing the selectivity by the adsorbent of one component C over component D, a ($\beta$) larger than 1.0 indicates preferential adsorption of component C within the adsorbent. A ($\beta$) less than 1.0 would indicate that component D is preferentially adsorbed leaving an unadsorbed phase richer in component C and an adsorbed phase richer in component D. Ideally, desorbent materials should have a selectivity equal to about 1 or slightly less than 1 with respect to all extract components so that all of the extract components can be desorbed as a class with reasonable flow rates of desorbent material, and so that extract components can displace desorbent material in a subsequent adsorption step. While separation of an extract component from a raffinate component is theoretically possible when the selectivity of the adsorbent for the extract component with respect to the raffinate component is greater than 1, it is preferred that such selectivity approach a value of 2. Like relative volatility, the higher the selectivity the easier the separation is to perform. Higher selectivities permit a smaller amount of adsorbent to be used.

Other important characteristics of the adsorbent are the rate of exchange of the extract component of the feed mixture with the desorbent material and the adsorptive capacity for the extract component. The exchange rate, i.e., the relative rate of desorption of the extract component-relates directly to the amount of desorbent material that must be employed in the process to recover the extract component from the adsorbent; faster rates of exchange reduce the amount of desorbent material needed to remove the extract component and therefore permit a reduction in the operating cost of the process. With faster rates of exchange, less desorbent material has to be pumped through the process and separated from the extract stream for reuse in the process. Capacity for adsorbing a specific volume of the extract component is essential—further, the greater the capacity, the less adsorbent is needed for a given separation.

The adsorbent may be employed in the form of a dense compact fixed bed which is alternatively contacted with the feed mixture and desorbent materials. In the simplest embodiment of the invention, the adsorbent is employed in the form of a single static bed in which case the process is only semicontinuous. In another embodiment, a set of two or more static beds may be employed in fixed-bed contacting with appropriate valving so that the feed mixture is passed through one or more adsorbent beds while the desorbent materials can be passed through one or more of the other beds in the set. The flow of feed mixture and desorbent materials may be either up or down through the desorbent. Any of the conventional apparatus employed in static bed countercurrent flow systems, however, have a much greater separation efficiency than fixed adsorbent bed systems and are therefore preferred. In the moving bed or simulated moving bed processes, the adsorption and desorption operations are continuously taking place which allows both continuous production of an extract and a raffinate stream and the continual use of feed and desorbent streams. One preferred embodiment of this process utilizes what is known in the art as the simulated moving bed countercurrent flow system. The operating principles and sequence of such a flow system are described in U.S. Pat. No. 2,985,589, incorporated by reference herein. In such a system, it is the progressive movement of multiple liquid access points down an adsorbent chamber that simulates the upward movement of adsorbent contained in the chamber. Only four of the access lines are active at any one time; the feed input stream, desorbent inlet stream, raffinate outlet stream, and extract outlet stream access lines. Coincident with this simulated upward movement of the solid adsorbent is the movement of the liquid occupying the void volume of the packed bed of adsorbent. So that countercurrent contact is maintained, a liquid flow down the adsorbent chamber may be provided by a pump. As an active liquid access point moves through a cycle, that is, from the top of the chamber to the bottom, the chamber circulation pump moves through different zones which require different flow rates. A programmed flow controller may be provided to set and regulate these flow rates.

The active liquid access points effectively divide the adsorbent chamber into separate zones, each of which has a different function. In this embodiment of our process, generally, three separate operational zones are present in order for the process to take place, although in some instances, an optional fourth zone may be used.

The adsorption zone, zone I, is defined as the adsorbent located between the feed inlet stream and the raffinate outlet stream. In this zone, the feedstock contacts the adsorbent, an extract component is adsorbed, and a raffinate stream is withdrawn. Since the general flow through zone I is from the feed stream which passes into the zone to the raffinate stream which passes out of the zone, the flow in this zone is considered to be a downstream direction when proceeding from the feed inlet to the raffinate outlet streams.

Immediately upstream with respect to fluid flow in zone I is the purification zone, zone II. The purification zone is defined as the adsorbent between the extract outlet stream and the feed inlet stream. The basic operations taking place in zone II are the displacement from the non-selective void volume of the adsorbent of any raffinate material carried into zone II by the shifting of adsorbent into this zone and the desorption of any raffinate material adsorbed within the selective pore volume of the adsorbent or adsorbed on the surfaces of the adsorbent particles. Purification is achieved by passing a portion of extract stream material leaving zone III into Zone II at zone II's upstream boundary, the extract outlet stream, to effect the displacement of raffinate material. The flow of material in zone II is in a downstream direction from the extract outlet stream to the feed inlet stream.

Immediately upstream of zone II with respect to the fluid flowing in zone II is the desorption zone III. The desorption zone is defined as the adsorbent between the desorbent inlet and the extract outlet stream. The function of the desorption zone is to allow a desorbent material which passes into this zone to displace the extract component which was adsorbed upon the adsorbent during a previous contact with feed in zone I in a prior cycle of operation. The flow of fluid in zone III is essentially in the same direction as that of zones I and II.

In some instances an optional buffer zone, zone IV, may be utilized. This zone, defined as the adsorbent between the raffinate outlet stream and the desorbent inlet stream, if used, is located immediately upstream with respect to the fluid flow to zone III. Zone IV would be utilized to conserve the amount of desorbent utilized in the desorption step since a portion of the raffinate stream which is removed from zone I can be passed into zone IV to displace desorbent material present in that zone out of that zone into the desorption zone. Zone IV will contain enough adsorbent so that raffinate material present in the raffinate stream passing out of zone I and into zone III can be prevented from passing into zone III thereby contaminating extract stream removed from zone III. In the instances in which the fourth operational zone is not utilized, the raffinate stream passed from zone I to zone IV must be carefully monitored in order that the flow directly from zone I to zone III can be stopped when there is an appreciable quantity of raffinate material present in the raffinate stream passing from zone I into zone III so that the extract outlet stream is not contaminated.

A cyclic advancement of the input and output streams through the fixed bed of adsorbent can be accomplished by utilizing a manifold system in which the valves in the manifold are operated in a sequential manner to effect the shifting of the input and output streams thereby allowing a flow of fluid with respect to solid adsorbent in a countercurrent manner. Another mode of operation which can effect the countercurrent flow of solid adsorbent with respect to fluid involves the use of a rotating disc valve in which the input and output streams are connected to the valve and the lines through which feed input, extract output, desorbent input and raffinate output streams are advanced in the same direction through the adsorbent bed. Both the manifold arrangement and disc valve are known in the art. Specifically rotary disc valves which can be utilized in this operation can be found in U.S. Pat. Nos. 3,040,777 and 3,422,848. Both of the aforementioned patents disclose a rotary type connection valve in which the suitable advancement of the various input and output streams from fixed sources can be achieved without difficulty.

In many instances, one operational zone will contain a much larger quantity of adsorbent than some other operational zone. For instance, in some operations, the buffer zone can contain a minor amount of adsorbent as compared to the adsorbent required for the adsorption and purification zones. It can also be seen that in instances in which desorbent is used which can easily desorb extract material from the adsorbent that a relatively small amount of adsorbent will be needed in a desorption zone as compared to the adsorbent needed in the buffer zone or adsorption zone or purification zone or all of them. Since it is not required that the adsorbent be located in a single column, the use of multiple chambers or a series of columns is within the scope of the invention.

It is not necessary that all of the input or output streams be simultaneously used, and in fact, in many instances some of the streams can be shut off while others effect an input or output of material. The apparatus which can be utilized to effect the process of this invention can also contain a series of individual beds connected by connecting conduits upon which are placed input or output taps to which the various input or output streams can be attached and alternately and periodically shifted to effect continuous operation. In some instances, the connecting conduits can be connected to transfer taps which during the normal operations do not function as a conduit through which material passes into or out of the process.

Although both liquid and vapor phase operations can be used in many adsorptive separation processes, liquid-phase operation is preferred for this process because of the lower temperature requirements and because of the higher yields of extract product that can be obtained with liquid-phase operation over those obtained with vapor-phase operation. Adsorption conditions will include a temperature range of from about 20° C. to about 200° C., with about 20° C. to about 100° C. being more preferred and a pressure range of from about atmospheric to whatever pressure is sufficient to insure liquid phase. Desorption conditions will include the same range of temperatures and pressures as used for adsorption conditions.

The size of the units which can utilize the process of this invention can vary anywhere from those of pilot plant scale (see for example our assignee's U.S. Pat. No. 3,706,812) to those of commercial scale and can range in flow rates from as little as a few cc an hour up to many thousands of gallons per hour.

A dynamic testing apparatus is employed to test various adsorbents with a particular feed mixture and desorbent material to measure the adsorbent characteristics of adsorptive capacity, selectivity and exchange rate. The apparatus consists of an adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Quantitative and qualitative analytical equipment such as refractometers, polarimeters and chromatographs can be attached to the outlet line of the chamber and used to detect quantitatively or determine qualitatively one or more components in the effluent stream leaving the adsorbent chamber. A pulse test, performed using this apparatus and the following general procedure, is used to determine selectivities and other data for various adsorbent systems. The adsorbent is filled to equilibrium with a particular desorbent material by passing the desorbent material through the adsorbent chamber. At a convenient time, a pulse of the complex petrochemical mixture, containing indene, is injected for a duration of several minutes. Desorbent flow is resumed, and the indene and other components are eluted as in a liquid-solid chromatographic operation. The effluent can be analyzed on stream or alternatively, effluent samples can be collected periodically and later analyzed separately by analytical equipment and traces of the envelopes of corresponding component peaks developed.

From information derived from the test, adsorbent performance can be rated in terms of void volume, retention volume for an extract or a raffinate component, selectivity for one component with respect to the other, and the rate of desorption of an extract component by the desorbent. The retention volume of an extract or a raffinate component may be characterized by the distance between the center of the peak envelope of an extract or a raffinate component and the peak envelope of the tracer component or some other known reference point. It is expressed in terms of the volume in cubic centimeters of desorbent pumped during this time interval represented by the distance between the peak envelopes. Selectivity, ($\beta$), for an extract component with respect to a raffinate component may be characterized by the ratio of the distance between the center of the extract component peak envelope and the tracer peak envelope (or other reference point) to the corresponding distance between the center of the raffinate component peak envelope and the tracer peak envelope. The rate of exchange of an extract component with the desorbent can generally be characterized by the width of the peak envelopes at half intensity. The narrower the peak width the faster the desorption rate. The desorption rate can also be characterized by the distance between the center of the tracer peak envelope and the disappearance of an extract component which has just been desorbed. This distance is again the volume of desorbent pumped during this time interval.

The following examples are presented to illustrate the selectivity relationship that makes the process of this invention possible. The examples are not intended to unduly restrict the scope of the claims.

EXAMPLE I

The purpose of this example is to present the results of a pulse test obtained from the above described pulse test apparatus when using a sodium-exchanged X zeolite at 120° C. with toluene as desorbent to separate and recover indene from an indene-containing complex petrochemical mixture.

A naphtha cracker pyrolysis oil was obtained with the following approximate composition:

| Component | Wt. % |
|---|---|
| $C_8$–$C_{10}$ alkyl aromatics | 46 |
| $C_8$–$C_{10}$ unsaturated aromatics | 31 |
| bicyclic aromatics and saturates | 4 |
| methyl indene | 5 |
| indene | 14 |

The $C_8$–$C_{10}$ alkyl aromatics include trimethylbenzenes such as pseudocumene and hemimellitene, indane, diethylbenzenes, propyltoluenes, and ethyldimethylbenzenes. The unsaturated aromatics include styrene, vinyltoluene isomers, alpha and beta methylstyrenes, and propenyltoluene isomers. Of this material, 95% boiled in the range 132°–208° C.

This material was vacuum fractionated in a Hypercal distillation column to yield an indene enriched midfraction. Gas chromatography/mass spectroscopy (GC/MS) analysis of the midfraction gave the following approximate composition:

| Component | Wt. % |
|---|---|
| $C_8$–$C_{10}$ alkyl aromatics | 21 |
| unsaturated alkyl aromatics | 13 |
| indene | 66 |

The alkyl aromatics contained in the indene-enriched midfraction include trimethylbenzenes, diethylbenzenes, ethyldimethylbenzenes, and propyltoluenes. The unsaturated aromatics include propenyl toluenes and methylstyrenes. Of this midfraction, boiled in the range 165°–196° C.

A feed pulse consisting of 1 cc of indene-enriched naphtha cracker pyrolysis oil midfraction, 1 cc toluene, and 0.25 cc n-heptane tracer was introduced to the pulse test column at 120° C., which was packed with NaX adsorbent having 4.84 wt. % water content. Toluene was used as the desorbent material at a flow rate of 1.2 cc/min.

Figure 1A:
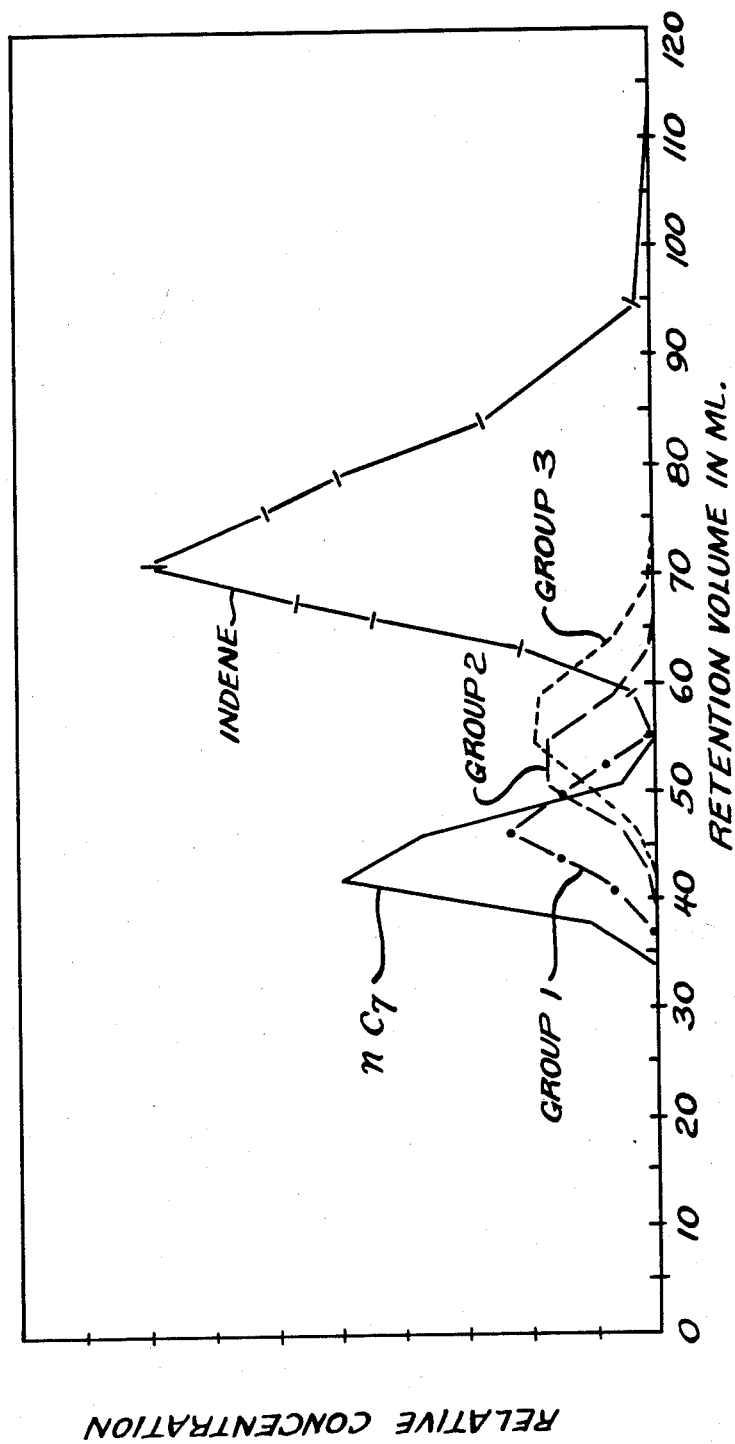
FIGS. 1 to 8 represent the results to the experiments described below in the Examples.

FIG. 1A illustrates the results of the experiment, in which group separation effects are observed. GC/MS analysis shows that the least adsorbed group of feed compounds consists of the alkyl benzenes and toluenes containing ethyl and propyl groups, such as diethyl benzenes and propyl toluenes. The second group has a longer retention on the adsorbent and consists of trimethylbenzenes such as pseudocumene, and methylstyrenes, such as beta methylstyrene, and other components of similar structure and functionality. The third group of compounds has yet longer retention volume and consists mainly of $C_{10}$ unsaturated alkyl aromatics such as propenyl toluene isomers. Finally, indene is the most strongly adsorbed material in the feed pulse mixture.

From the plot of relative concentration (by gas chromatographic area counts) vs. retention volume (RV) in ml. shown in FIG. 1A, selectivities can be calculated among the various groups of compounds and indene:

| Component | Half Width | Net RV | Selectivity ($\beta$) |
|---|---|---|---|
| n-$C_7$ | 8.4 | 0 | tracer |
| group 1 | 8.1 | 3.3 | 9.10 |
| group 2 | 10.5 | 9.1 | 3.28 |
| group 3 | 12.9 | 12.7 | 2.35 |
| indene | 15.7 | 29.9 | reference |

Figure 1B:
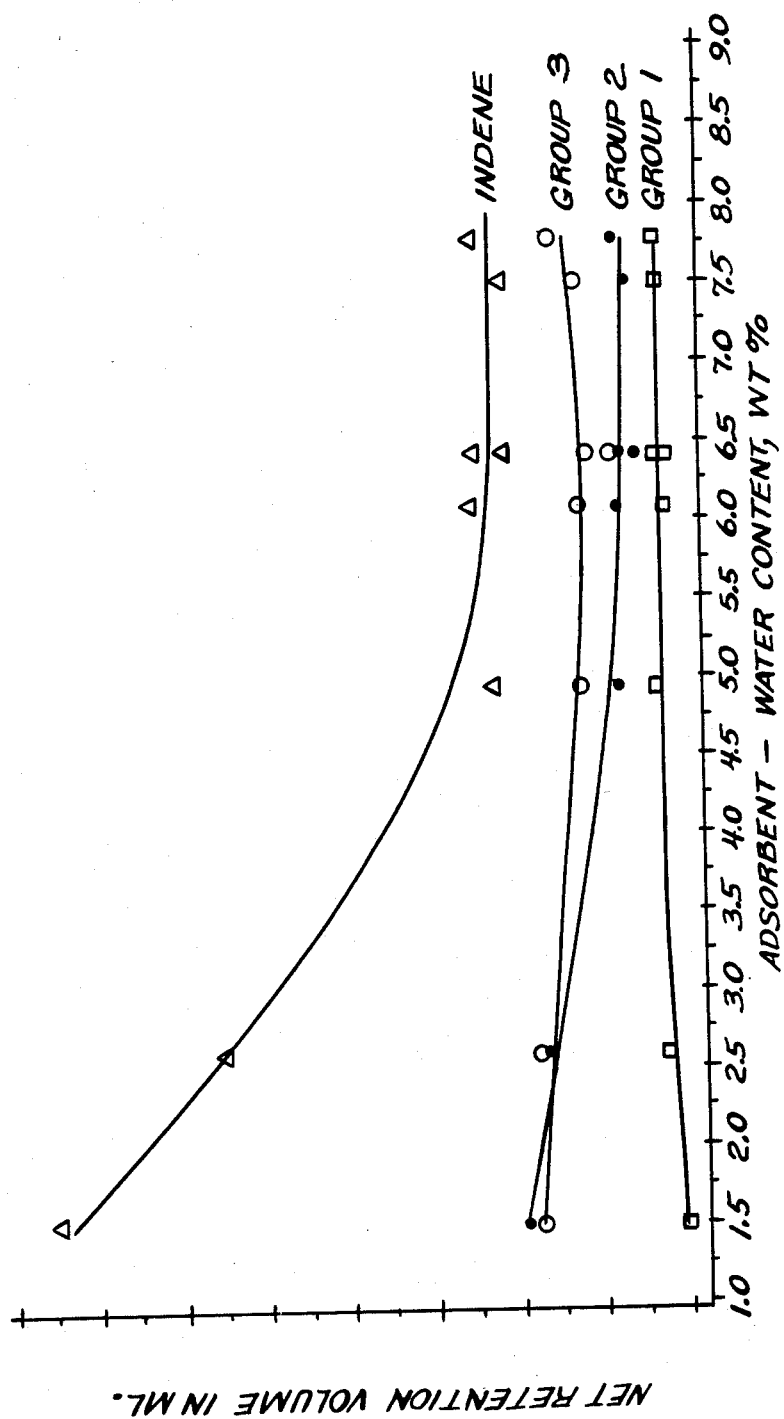

The effect of adsorbent water content can be discerned by repeating the experiment of Example I using adsorbents with varying water wt. % values. FIG. 1B is a plot f component net retention volume (NRV) versus adsorbent wt. % water. It is observed that, while separation and recovery of indene is satisfactory over the entire range of adsorbent water content, selectivity increases as water concentration is reduced and NRV of indene and component groups 2 and 3 increase. The increase in NRV means longer desorption times, so that the two factors must be balanced for optimum economic operation.

EXAMPLE II

Figure 2:
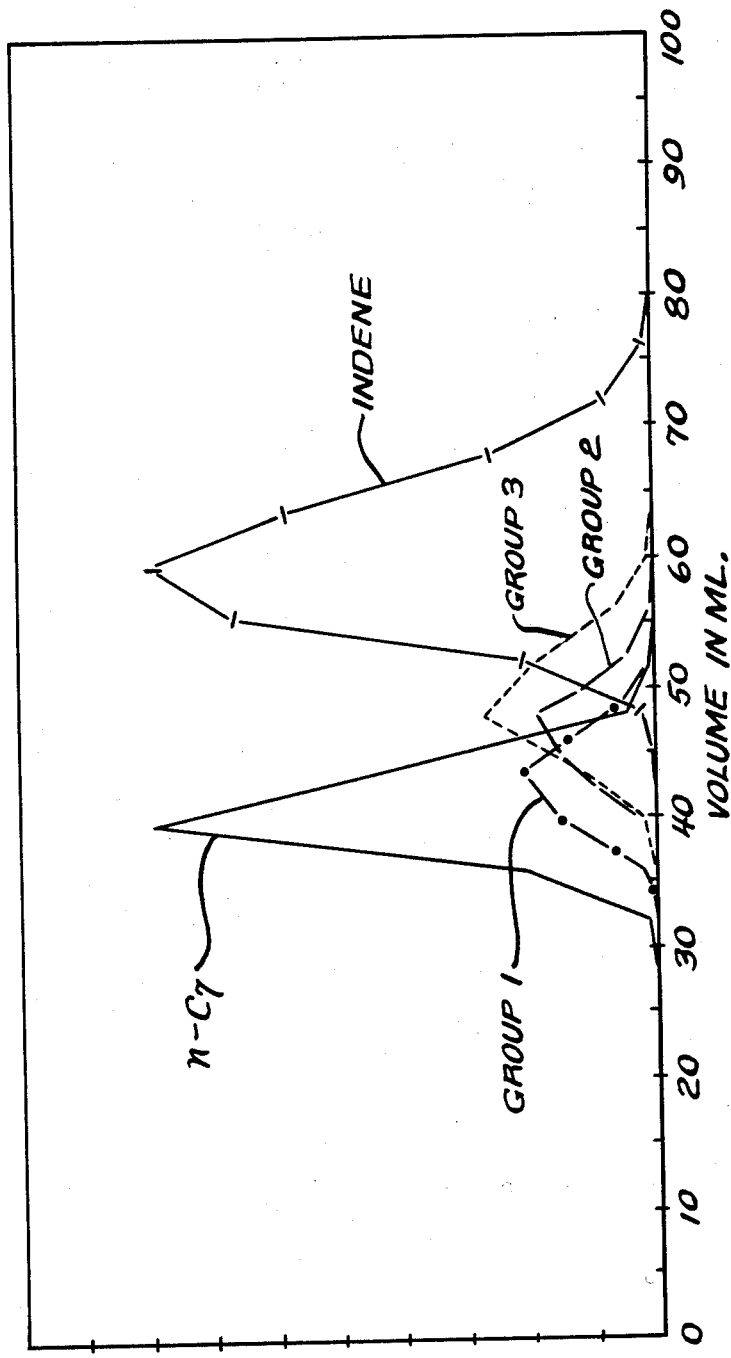

The pulse experiment of Example 1 was repeated except that the NaX adsorbent contained 6.14 wt. % water and the desorbent material was benzene. FIG. 2 shows the results, and the selectivities are given in the following table:

| Component | Half Width | Net RV | Selectivity ($\beta$) |
| --- | --- | --- | --- |
| n-C$_7$ | 6.8 | 0 | tracer |
| group 1 | 8.3 | 2.0 | 9.60 |
| group 2 | 8.3 | 5.8 | 3.31 |
| group 3 | 9.5 | 8.2 | 2.34 |
| indene | 12.4 | 19.2 | reference |

EXAMPLE III

Figure 3:
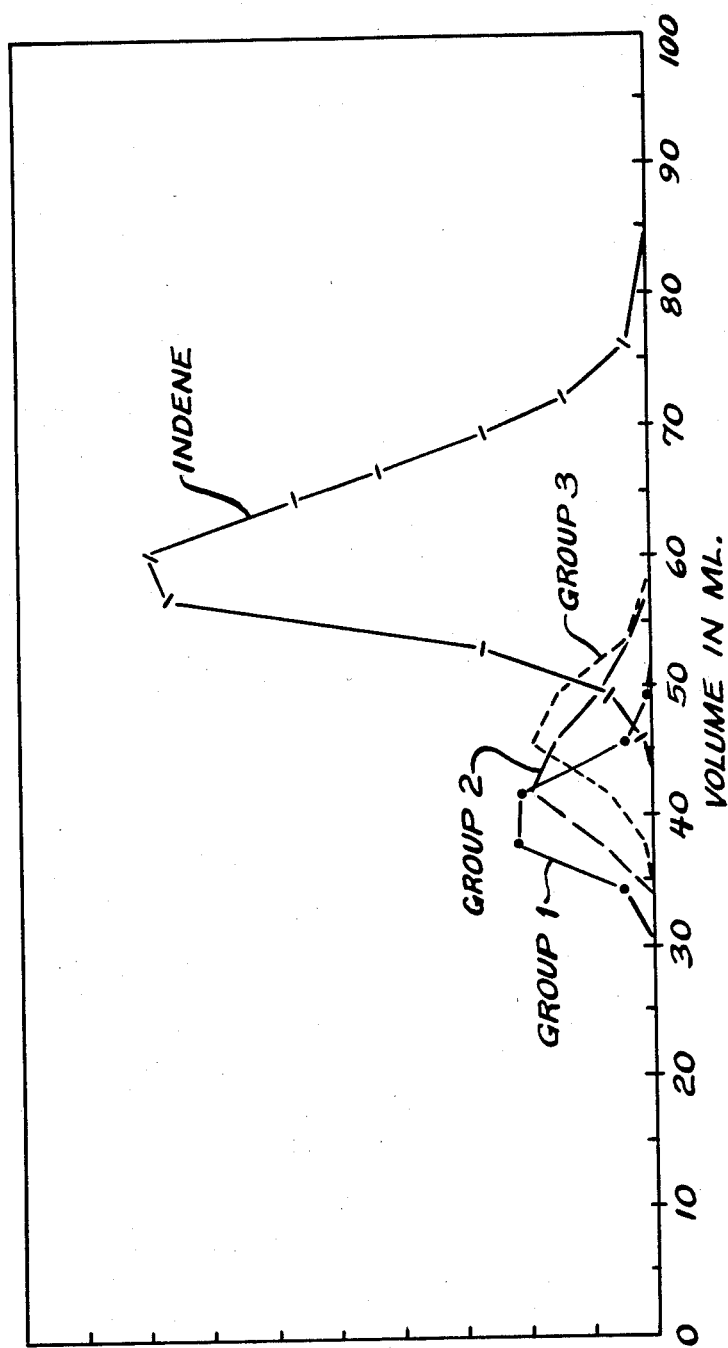

The pulse experiment of Example 1 was repeated except that the NaX adsorbent contained approximately 1.5 wt. % water and the desorbent was fluorobenzene. N-C$_7$ was omitted from the feed. The results are shown in FIG. 3 and the following table:

| Component | Half Width | Net RV | Selectivity ($\beta$) |
| --- | --- | --- | --- |
| group 1 | 8.6 | 0 | tracer |
| group 2 | 10.5 | 3.7 | 5.59 |
| group 3 | 8.7 | 7 | 2.95 |
| indene | 13.2 | 20.7 | reference |

EXAMPLE IV

Figure 4:
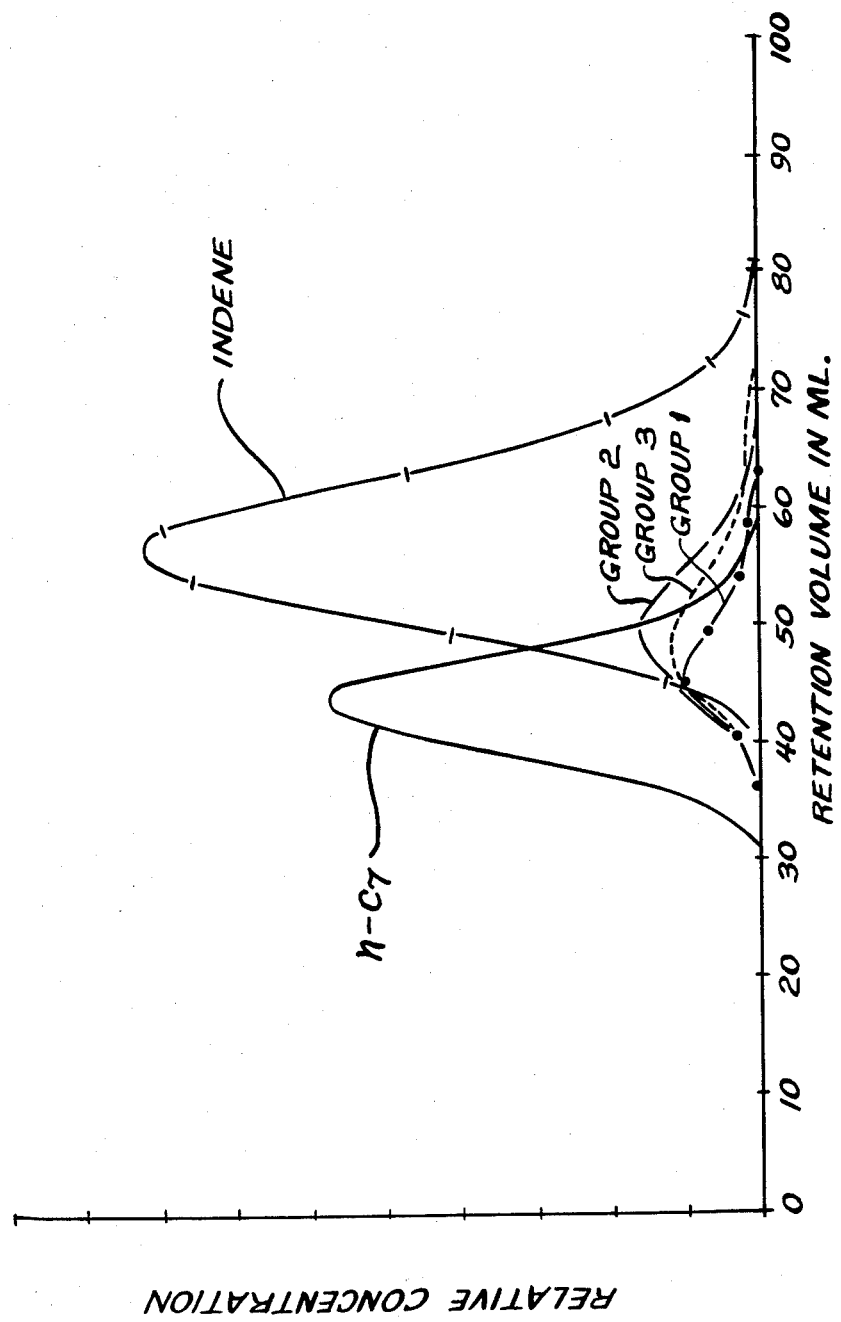

The pulse experiment of Example I was repeated except that the adsorbent was NaY zeolite which contained about 0.06 wt. % water and the temperature was 60° C. The results are shown in FIG. 4 and the following table, from which it can be noted that the Group 2 and Group 3 compounds are more similar in separation behavior than when NaX adsorbent is used:

| Component | Half Width | Net RV | Selectivity ($\beta$) |
| --- | --- | --- | --- |
| n-C$_7$ | 10.3 | 0 | tracer |
| group 1 | 9.8 | 3.3 | 4.11 |
| group 2 | 13.0 | 6.6 | 2.06 |
| group 3 | 13.5 | 5.7 | 2.35 |
| indene | 15.2 | 13.5 | reference |

EXAMPLE V

Figure 5:
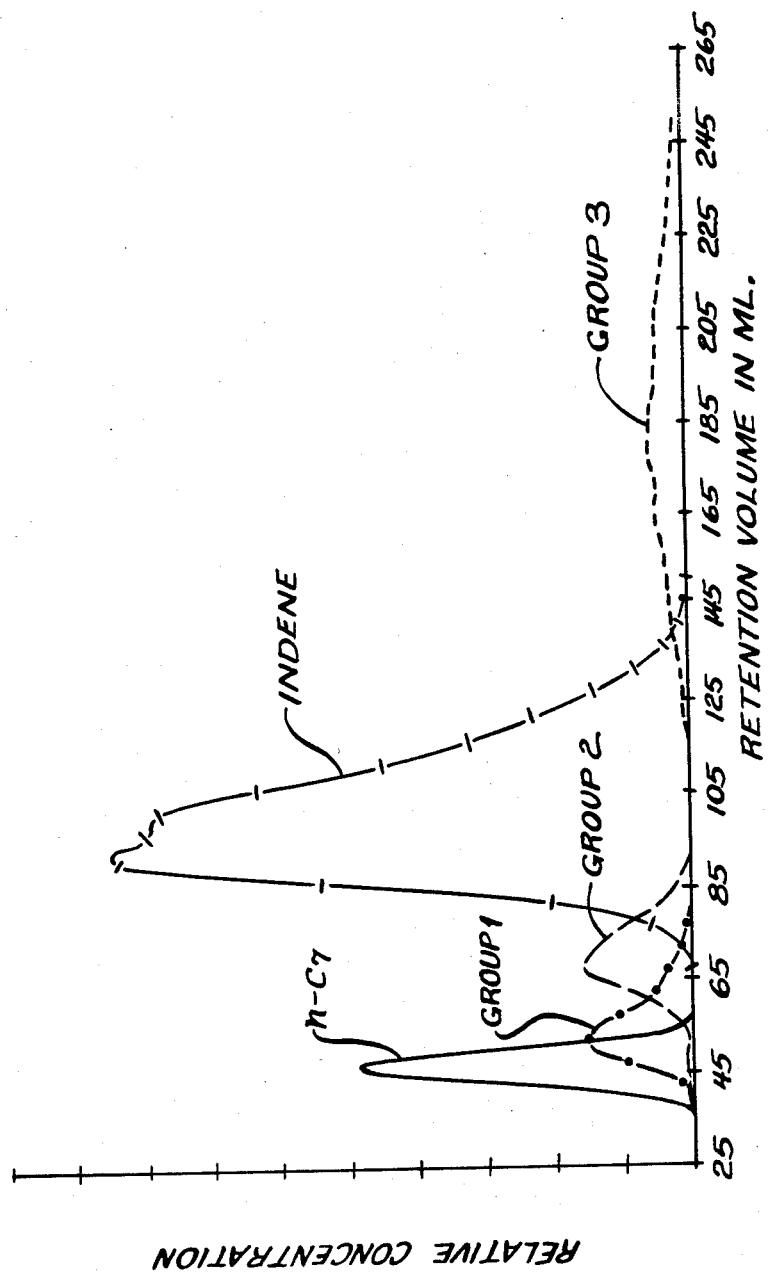

The pulse experiment of Example I was repeated except that the adsorbent was K-X zeolite containing approximately 1.5 wt. % water and the temperature was 60° C. The results of this experiment are given in FIG. 5 and the following table, from which it is clear that indene is separated from the alkyl aromatics and unsaturated alkyl aromatics of Groups 1 and 2, and from the strongly retained unsaturated alkyl aromatics of Group 3:

| Component | Half Width | Net RV | Selectivity ($\beta$) |
| --- | --- | --- | --- |
| n-C$_7$ | 7.8 | 0 | tracer |
| group 1 | 13.8 | 6.6 | 7.98 |
| group 2 | 16.8 | 23.7 | 2.22 |
| group 3 | 73.7 | 139.5 | 0.38 |

-continued

| Component | Half Width | Net RV | Selectivity ($\beta$) |
| --- | --- | --- | --- |
| indene | 28.0 | 52.6 | reference |

EXAMPLE VI

Figure 6:
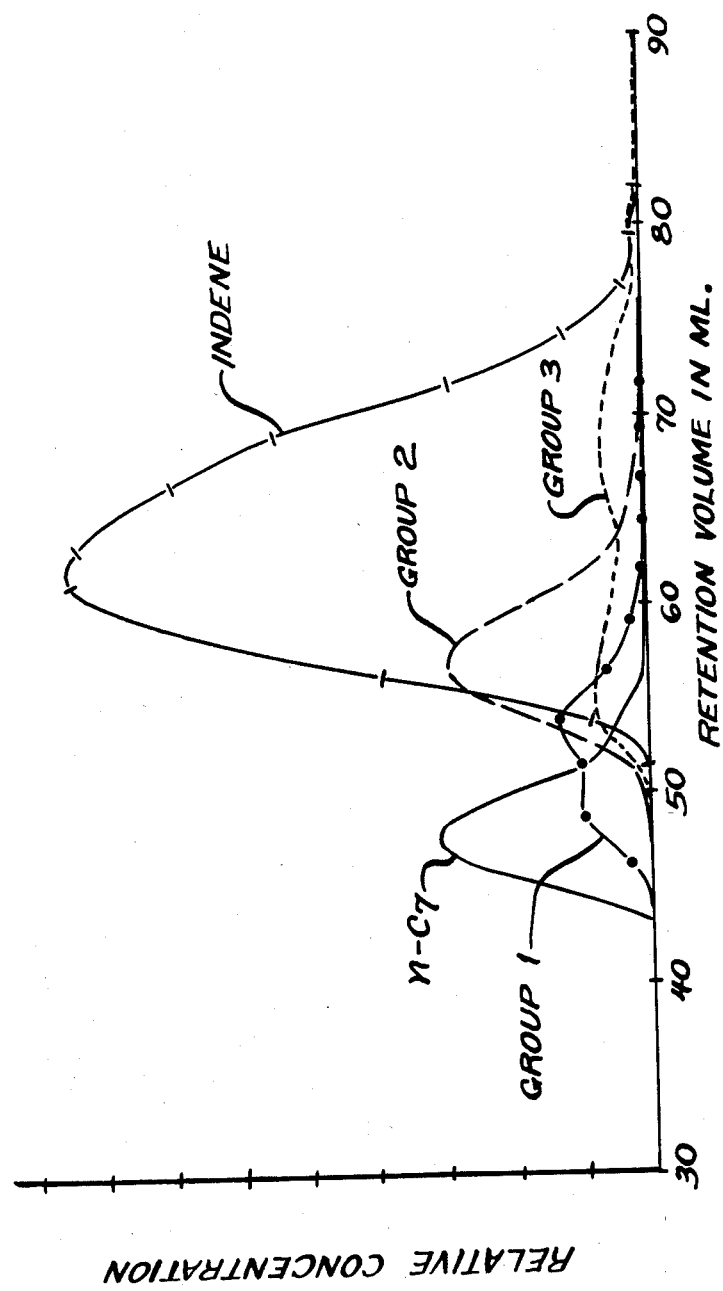

The pulse experiment of Example 1 was repeated except that the adsorbent was potassium-exchanged Y zeolite containing approximately 1 wt. % water and the temperature was 60° C. The results of this experiment are given in FIG. 6 and the following table, from which it is clear that indene is separated from alkyl aromatics and unsaturated alkyl aromatics, although not as completely as in the previous examples:

| Component | Half Width | Net RV | Selectivity ($\beta$) |
| --- | --- | --- | --- |
| n-C$_7$ | 5.8 | 0 | tracer |
| group 1 | 8.5 | 4.0 | 3.86 |
| group 2 | 7.2 | 9.3 | 1.66 |
| group 3 | 21.3 | 15.0 | 0.73 |
| indene | 13.7 | 15.7 | reference |

EXAMPLE VII

Figure 7:
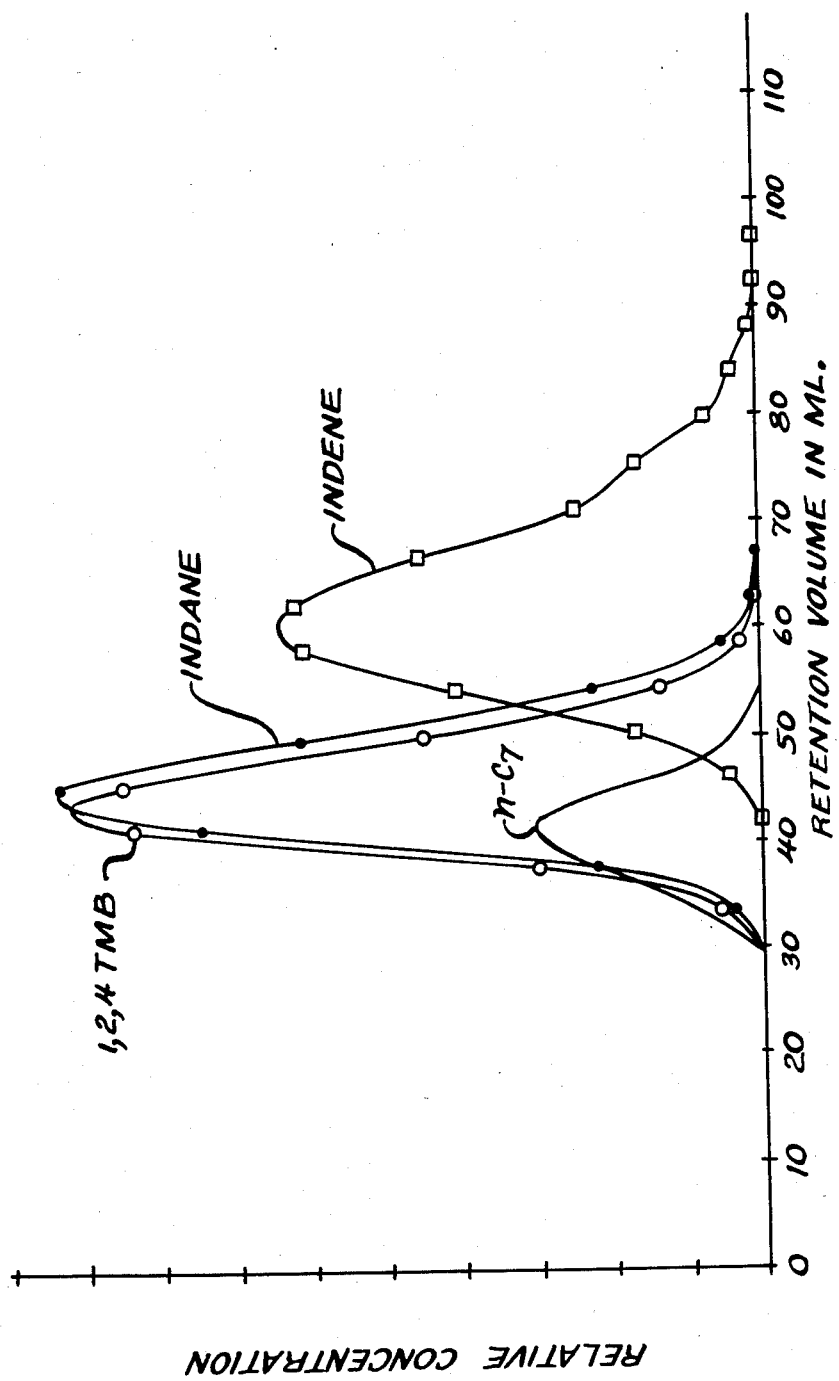

The pulse experiment of Example I was repeated except that the NaX adsorbent contained approximately 7.5 wt. % water. and the feed consisted of 20 vol. % each indane, indene, and 1,2,4-trimethylbenzene, 10 vol. % n-C7 tracer, and 30 vol. % toluene, and the temperature was 60° C. The results of this experiment, shown in FIG. 7 and the following table, indicate the separation of indene from simple alkyl aromatic mixtures, such as may be encountered in the synthetic preparation of indene from hydrocarbon precursors via dehydrogenation and/or cyclization reactions:

| Component | Half Width | Net RV | Selectivity ($\beta$) |
| --- | --- | --- | --- |
| n-C$_7$ | 10.1 | 0 | tracer |
| 1,2,4-TMB | 11.9 | 4.1 | 5.10 |
| indane | 12.2 | 5.2 | 4.01 |
| indene | 17.2 | 20.8 | reference |

EXAMPLE VIII

This example illustrates the ability of my process, when operated in a preferred embodiment, which utilizes a continuous simulated moving bed countercurrent type of operation, and comprises a pilot plant scale testing apparatus known as a carousel unit described in detail in deRosset et al. U.S. Pat. No. 3,706,812, incorporated herein by reference. Briefly, the apparatus consists essentially of 24 serially connected adsorbent chambers having about 44 cc volume each. Total chamber volume of the apparatus is approximately 1,056 cc. The individual adsorbent chambers are serially connected to each other with relatively small diameter connecting piping and to a rotary type valve with other piping. The valve has inlet and outlet ports which direct the flow of feed and desorbent material to the chambers and extract and raffinate streams from the chambers. By manipulating the rotary valve and maintaining given pressure differentials and flow rates trough the various lines passing into and out of the series of chambers, a simulated countercurrent flow is produced. The adsorbent remains stationary while fluid flows throughout the serially connected chambers in a manner which when viewed from any position within the adsorbent chambers is steady countercurrent flow. The moving of the rotary valve is done in a periodic shifting manner to allow a new operation to take place in the adsorbent beds located between the active inlet and outlet ports of the rotary valve. Attached to the rotary valve are input lines and output lines through which fluids to and from the process flow. The rotary valve contains a feed input line through which passes the feed mixture, and extract stream outlet line through which passes the desorbent material, i.e., toluene, in admixture with indene, a desorbent material inlet line through which passes desorbent materials and a raffinate stream outlet line through which passes alkyl and unsaturated aromatics in admixture with desorbent material. Additionally, a flush material inlet line is used to admit flush material for the purpose of flushing feed components from lines which had previously contained feed material and which will subsequently contain the raffinate or extract stream. The flush material employed is toluene which then leaves the apparatus as part of the extract stream and raffinate stream. Additional apparatus details can be found in U.S. Pat. No. 3,706,812. In order to better understand the operations taking place within the apparatus reference can be made to D. B. Broughton, U.S. Pat. No. 2,985,589 and to D. B. Broughton et al., "The Separation of P-Xylene from $C_8$ Hydrocarbon Mixtures by the Parex Process," presented at the Third Joint Annual Meeting, American Institute of Chemical Engineers and Puerto Rican Institute of Chemical Engineers, San Juan, Puerto Rico, May 17 through May 20, 1970. These references describe in detail the basic operations taking place in the testing apparatus used in this embodiment, and although said references are concerned with the separation of hydrocarbons, the testing apparatus itself is perfectly suited for purposes of this embodiment.

The feed mixture to the apparatus was a fractionated heavy naphtha cracker pyrolysis oil containing 70.5% indene. The adsorbent used was the sodium-exchanged Y faujasite of Example IV. The desorbent was toluene.

The operating parameters of the carousel Unit were as follows:
1. A/F=3, where A is the selective pore volume of the adsorbent in cc and F is the feed rate to the separation stage in cc/hr.
2. Process temperature=60° C.
3. Valve cycle time=60 min.

A number of experiments, each of six hours duration, were conducted on the carousel unit. In these experiments, it was observed that indene was adsorbed and separated to form the extract, while the alkyl and unsaturated aromatics were relatively unadsorbed and were separated to form the raffinate.

Figure 8:
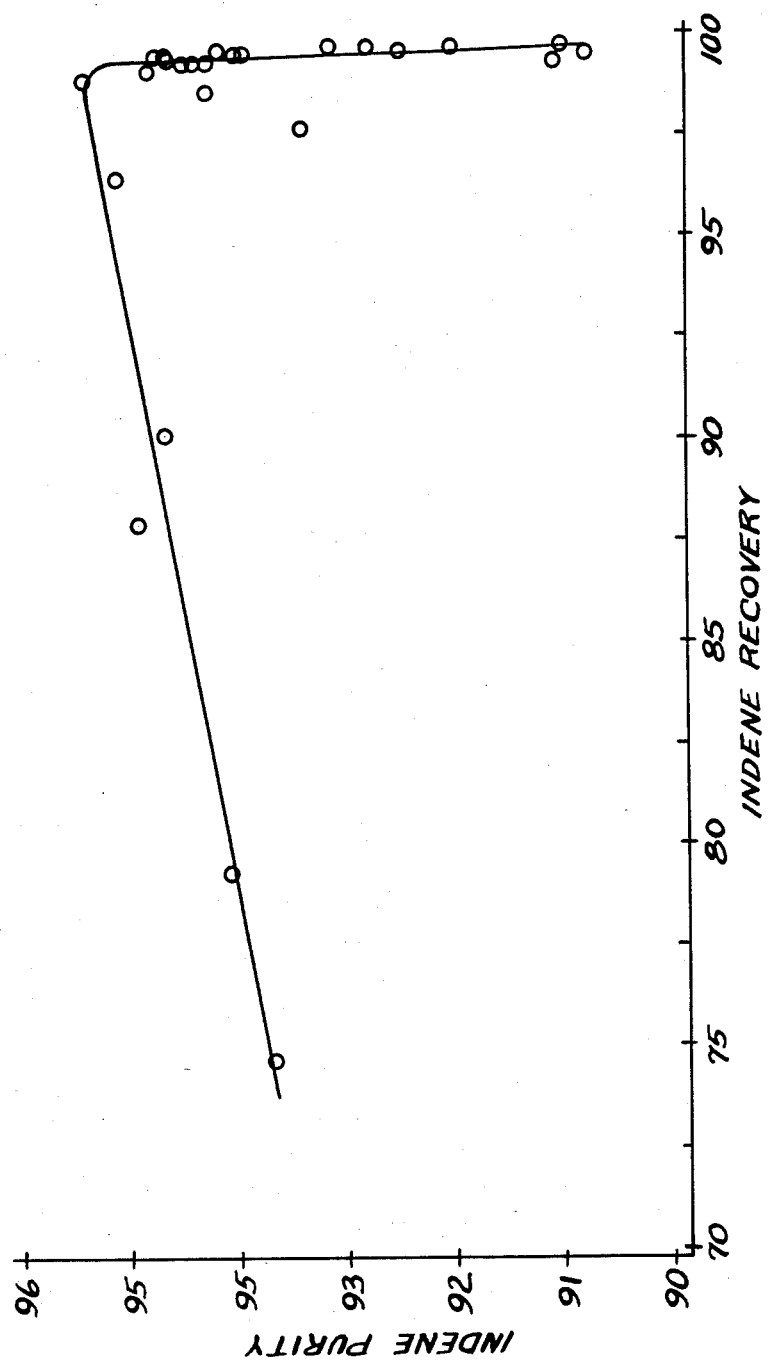

In these experiments, the extract and raffinate streams were analyzed for their component concentrations. The results of these experiments can be plotted as a curve of indene extract purity versus indene recovery and are illustrated in FIG. 8. The best separation performance obtained was 95.4% indene purity at 99% recovery.

Thus, it is clear from the above that the use of a NaY adsorbent enables the separation of indene from a complex petrochemical mixture containing alkyl aromatics, unsaturated alkyl aromatics, and indene.

Since the effects of different operating conditions on the product purity and yield have not been completely investigated, the results of the above tests are not intended to represent the optimums that might be achieved.

Water concentration (wt. %) of the adsorbent is determined by LOI method (loss on ignition at 500° C.).

What is claimed is:

1. A process for separating indene from a feed mixture comprising alkyl aromatics, unsaturated alkyl-substituted aromatic and indene comprising contacting said feed mixture at adsorption conditions with an X or Y type zeolite exchanged with sodium or potassium ions to selectively adsorb indene and recovering said indene by desorption at desorption conditions with a desorbent selected from the group consisting of benzene and halogen- and alkyl-substituted monocyclic aromatics.

2. The process of claim 1, wherein the water content of said X-type adsorbent is less than 8 wt. % (LOI).

3. The process of claim 2 wherein said water content is from 4-7 wt. %.

4. The process of claim 1 wherein said feed mixture is a petrochemical material distilled to obtain a midcut fraction having an indene concentration of 30-80 wt. %.

5. The process of claim 1 wherein the concentration of indene in said feed mixture is less than 35 wt. %.

6. The process of claim 1 wherein said feed is a fraction of a petrochemical material.

7. The process of claim 1 wherein said feed is a vacuum fractioned naphtha cracker pyrolysis oil.

8. The process of claim 1 wherein said feed additionally contains indane.

9. The process of claim 1 wherein said desorbent is toluene.

10. The process of claim 1 wherein said desorbent is fluorobenzene.

* * * * *

UNITED STATES PATENT AND TRADEMARK OFFICE
CERTIFICATE OF CORRECTION

PATENT NO. : 4,827,077
DATED : May 2, 1989
INVENTOR(S) : Zinnen

It is certified that error appears in the above-identified patent and that said Letters Patent is hereby corrected as shown below:

In Column 14, line 26: Delete "type".

Signed and Sealed this

Twenty-sixth Day of December, 1989

*Attest:*

JEFFREY M. SAMUELS

*Attesting Officer*     Acting Commissioner of Patents and Trademarks